United States Patent
Zhang (10) Patent No.: US 11,586,809 B2
(45) Date of Patent: Feb. 21, 2023

(54) METHOD AND APPARATUS FOR RECOGNIZING MEDICAL ENTITY IN MEDICAL TEXT

(71) Applicant: BOE TECHNOLOGY GROUP CO., LTD., Beijing (CN)

(72) Inventor: Zhenzhong Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 971 days.

(21) Appl. No.: 16/316,468

(22) PCT Filed: Apr. 24, 2018

(86) PCT No.: PCT/CN2018/084214
§ 371 (c)(1),
(2) Date: Jan. 9, 2019

(87) PCT Pub. No.: WO2019/015369
PCT Pub. Date: Jan. 24, 2019

(65) Prior Publication Data
US 2021/0342539 A1  Nov. 4, 2021
US 2022/0300710 A9  Sep. 22, 2022

(30) Foreign Application Priority Data

Jul. 20, 2017  (CN) .......................... 201710594503.X (51) Int. Cl.
*G06F 40/20*  (2020.01)
*G06F 40/253*  (2020.01)
(Continued)

(52) U.S. Cl.
CPC ............ *G06F 40/20* (2020.01); *G06F 40/169* (2020.01); *G06F 40/253* (2020.01);
(Continued)

(58) Field of Classification Search
CPC .......... G06F 40/00; G06F 40/10; G06F 40/12; G06F 40/126; G06F 40/129;
(Continued)

(56) References Cited

U.S. PATENT DOCUMENTS 8,457,950 B1 * 6/2013 Gardner .............. G10L 15/1815
704/10
9,129,013 B2 * 9/2015 Delaney .................. G06F 40/30
(Continued)

FOREIGN PATENT DOCUMENTS

| CN | 104965992 A | 10/2015 |
| CN | 105894088 A | 8/2016 |

(Continued)

OTHER PUBLICATIONS

Ma et al., "Dependency based convolutional neural networks for sentence embedding", Proceedings of 53rd Annual Meetings of the Association for Computational Linguistics, pp. 174-179, Jul. 26-31, 2015.*

(Continued)

*Primary Examiner* — Richard Z Zhu
(74) *Attorney, Agent, or Firm* — Armstrong Teasdale LLP (57) ABSTRACT

Embodiments of the present disclosure provide a method and an apparatus for recognizing a medical entity in a medical text. In this method, the medical text is segmented into a plurality of words. Each of the words is used as a target word. A local and a global annotation feature of the target word are determined. The local annotation feature includes the target word. The global annotation feature includes a relationship between the target word and the recognized medical entity. Next, a label for the target word is determined from candidate labels based on the local and global annotation feature. Next, a combination relationship between the target word and a previous word of the target (Continued)

word is obtained based on the label for the target word. The combination relationship includes combination and non-combination. Next, the combined words are recognized as the medical entity based on the combination relationship.

18 Claims, 3 Drawing Sheets

(51) Int. Cl.
*G06F 40/268* (2020.01)
*G06F 40/169* (2020.01)
*G06F 40/295* (2020.01)
*G16H 50/70* (2018.01)
*G06N 7/00* (2023.01)
G06F 40/284 (2020.01)
G06F 40/30 (2020.01)
G06F 40/289 (2020.01)
G06F 40/279 (2020.01)

(52) U.S. Cl.
CPC .......... *G06F 40/268* (2020.01); *G06F 40/295* (2020.01); *G06N 7/005* (2013.01); *G16H 50/70* (2018.01); *G06F 40/279* (2020.01); *G06F 40/284* (2020.01); *G06F 40/289* (2020.01); *G06F 40/30* (2020.01)

(58) Field of Classification Search
CPC .... G06F 40/131; G06F 40/166; G06F 40/169; G06F 40/20; G06F 40/211; G06F 40/216; G06F 40/279; G06F 40/284; G06F 40/289; G06F 40/295; G06F 40/30; G06F 16/288
See application file for complete search history.

(56) References Cited

U.S. PATENT DOCUMENTS

| | | | | |
|---|---|---|---|---|
| 10,380,259 | B2* | 8/2019 | Lee | G06F 40/30 |
| 10,509,814 | B2* | 12/2019 | Lastra Diaz | G06F 16/24522 |
| 10,754,925 | B2* | 8/2020 | D'Souza | G16H 40/20 |
| 2009/0249182 | A1 | 10/2009 | Symington et al. | |
| 2011/0270604 | A1* | 11/2011 | Qi | G06F 16/3344 704/9 |

FOREIGN PATENT DOCUMENTS

| | | |
|---|---|---|
| CN | 106202054 A | 12/2016 |
| CN | 106407443 A | 2/2017 |
| CN | 106446526 A | 2/2017 |
| CN | 106776711 A | 5/2017 |
| CN | 106844351 A | 6/2017 |
| CN | 106844723 A | 6/2017 |
| CN | 106845061 A | 6/2017 |
| EP | 1617340 A2 | 1/2006 |
| JP | 200631010 A | 2/2006 |
| JP | 2007094459 A | 4/2007 |
| JP | 2015158738 A | 9/2015 |
| WO | WO-2017217489 A1 * | 12/2017 ......... G06F 16/3344 |

OTHER PUBLICATIONS

WO2017217489 A1 (Year: 2017).*
Yang Chenhao, "Research and Platform Development on Chinese Electronic Medical Records Entity Assertion and Relation Extraction Based on Deep Learning", 2016, 66 pages.: with English translation of relevant part.
China First Office Action, Application No. 201710594503.X, dated Dec. 27, 2019, 17 pps.: with English translation.
Yang Yang, "Experimental Study on Semantic Relationships of Clinical Nomenclature of Traditional Chinese Medicine", 2007, 96 pages.: with English translation of relevant part.
Yang Jin-Feng et al., "Corpus Construction for Named Entities and Entity Relations on Chinese Electronic Medical Records", Journal of Software, 2016, 27(11):2725-2746, 48 pages.: with English translation of relevant part.
Yang Chenhao, "Research and Platform Development on Chinese Electronic Medical Records Entity Assertion and Relation Extraction Based on Deep Learning", 2016, 58 pages.: with English translation of relevant part.
PCT International Search Report, Application No. PCT/CN2018/084214, dated Jul. 20, 2018, 6 pages: with English translation.
PCT Written Opinion, Application No. PCT/CN2018/084214, dated Jul. 20, 2018, 7 pages.: with English translation of relevant part.
European Extended Search Report, Application No. 18826482.4, dated Mar. 15, 2021, 11 pps.
Tang Buzhou et al., "Recognizing Disjoint Clinical Concepts in Clinical Text Using Machine Learning-based Methods", Annual Symposium proceedings, XP055781787, Jan. 1, 2015, pp. 1184-1193.
Tang Buzhou et al., "Clinical Entity Recognition Using Structural Support Vector Machines With Rich Features", Proceedings of the ACM Sixth International Workshop on Data and Text Mining in Biomedical Informatics, XP055781842, Jan. 1, 2012, 7 pps.
Lin Yao et al., "Biomedical Named Entity Recognition Based on Deep Neutral Network", International Journal of Hybrid Information Technology, vol. 8, No. 8, Aug. 31, 2015, XP055781681, pp. 279-288.
Japanese Notice of Reasons for Refusal, Application No. 2018567241, dated Aug. 11, 2021, 6 pps.: with English translation.

* cited by examiner

METHOD AND APPARATUS FOR RECOGNIZING MEDICAL ENTITY IN MEDICAL TEXT

CROSS REFERENCE TO RELATED APPLICATIONS

This patent application is a National Stage Entry of PCT/CN2018/084214 filed on Apr. 24, 2018, which claims the benefit and priority of Chinese Patent Application No. 201710594503.X filed on Jul. 20, 2017, the disclosures of which are incorporated by reference herein in their entirety as part of the present application.

BACKGROUND

The present disclosure relates to the field of medical data processing technologies, and more particularly, to a method and an apparatus for recognizing a medical entity in a medical text.

With the development of medical information technologies, a large number of available electronic medical texts (such as electronic medical records and medical examination reports, etc.) have appeared. These medical texts are used to support clinical decision systems. However, since the electronic medical texts are mostly written in natural languages, useful information in the electronic medical texts cannot be directly used by the clinical decision systems that rely on structured data. In order to make full use of the electronic medical texts, natural language processing technologies capable of extracting the structured data from the natural languages attract extensive attention in the field of clinical medicine. As a basic task of clinical natural language processing, recognition of medical entities has always attracted extensive attention by the medical community. The medical entities typically contain words related to drugs, problems (including diseases and symptoms), examinations and treatments. The medical entities include continuous medical entities (medical entities made up of continuous words) and discontinuous medical entities (medical entities made up of discontinuous words).

BRIEF DESCRIPTION

Embodiments described herein provide a method and an apparatus for recognizing a medical entity in a medical text.

A first aspect of the present disclosure provides a method and an apparatus for recognizing a medical entity in a medical text. In this method, the medical text is segmented into a plurality of words. Each of the plurality of words is used as a target word. A local annotation feature and a global annotation feature of the target word are determined for the target word. The local annotation feature includes the target word. The global annotation feature includes a relationship between the target word and the recognized medical entity. Next, a label for the target word is determined from a plurality of candidate labels based on the local annotation feature and the global annotation feature of the target word. Next, a combination relationship between the target word and a previous word of the target word is obtained based on the label for the target word. The combination relationship includes combination and non-combination. Next, the combined words are recognized as the medical entity based on the combination relationship.

In some embodiments of the present disclosure, the plurality of candidate labels include a first label, a second label, a third label, a fourth label, and a fifth label. The first label is configured to indicate that the word is a shared beginning portion of the medical entity. The second label is configured to indicate that the word is an unshared beginning portion of the medical entity. The third label is configured to indicate that the word is a successive portion of the medical entity. The fourth label is configured to indicate that the word is a portion of a nonmedical entity and that an operation of medical entity recognition is to be performed. The fifth label is configured to indicate that the word is a portion of the nonmedical entity and that the operation of medical entity recognition is not performed.

In some embodiments of the present disclosure, in the step of determining the label for the target word from the plurality of candidate labels based on the local annotation feature and the global annotation feature of the target word, for each of the plurality of candidate labels, a probability that the candidate label is the label for the target word is calculated based on the local annotation feature and the global annotation feature of the target word. Next, the candidate label with a highest probability is determined as the label for the target word.

In some embodiments of the present disclosure, the probability is calculated using a maximum entropy model.

In some embodiments of the present disclosure, in the step of obtaining the combination relationship between the target word and the previous word of the target word based on the label for the target word, if the label is the first label, the label and a previous label of the label are not combined. If the label is the third label, the label and one of a previous first label, a previous second label and a previous third label of the label are combined. If the label is the second label, a combination feature of the target word and a combination feature of a previous word of the target word having the first label or the second label are determined, wherein the combination feature includes a morpheme contained in the corresponding word. A label combination probability and a label non-combination probability are calculated based on the combination feature of the target word and the combination feature of the previous word of the target word having the first label or the second label. If the label combination probability is greater than the label non-combination probability, the second label and a previous first label or a previous second label of the second label are combined. If the label combination probability is not greater than the label non-combination probability, the second label and the previous first label or the previous second label of the second label are not combined. If the label is the fourth label, the label and the previous label of the label are not combined and the operation of medical entity recognition is performed. If the label is the fifth label, the label and the previous label of the label are not combined, and the combination relationship between the words corresponding to the labels is determined based on the combination of the labels.

In some embodiments of the present disclosure, the local annotation feature further includes X previous words of the target word and X posterior words of the target word, wherein X is a natural number.

In some embodiments of the present disclosure, the local annotation feature further includes a part of speech of the target word, parts of speech of the X previous words of the target word, and parts of speech of the X posterior words of the target word.

In some embodiments of the present disclosure, the global annotation feature further includes a relationship between Y previous words of the target word and the recognized medical entity and a relationship between Y posterior words of the target word and the recognized medical entity, wherein Y is a natural number.

In some embodiments of the present disclosure, the global annotation feature includes whether the target word being contained in the recognized medical entity, whether the Y previous words of the target word being contained in the recognized medical entity, and whether the Y posterior words of the target word being contained in the recognized medical entity.

In some embodiments of the present disclosure, the combination feature further includes morphemes contained in Z previous words of the corresponding word and morphemes contained in Z posterior words of the corresponding word, wherein Z is a natural number.

In some embodiments of the present disclosure, the combination feature includes morphemes contained in the corresponding word, Z previous words of the corresponding word, Z posterior words of the corresponding word, morphemes contained in the Z previous words of the corresponding word, and morphemes contained in the Z posterior words of the corresponding word.

In some embodiments of the present disclosure, the label combination probability and the label non-combination probability are calculated using a maximum entropy model.

In some embodiments of the present disclosure, the maximum entropy model is trained using an optimization algorithm.

A second aspect of the present disclosure provides an apparatus for recognizing a medical entity in a medical text. The apparatus includes at least one processor and at least one memory storing a computer program. When the computer program is executed by the at least one processor, the apparatus is caused to segment the medical text into a plurality of words, perform the following operations on each of the plurality of words as a target word: determine a local annotation feature and a global annotation feature of the target word, wherein the local annotation feature includes the target word, and the global annotation feature includes a relationship between the target word and a recognized medical entity, determine a label for the target word from a plurality of candidate labels based on the local annotation feature and the global annotation feature of the target word, obtain a combination relationship between the target word and a previous word of the target word based on the label for the target word, wherein the combination relationship includes combination and non-combination, and recognize the combined word as the medical entity based on the combination relationship.

A third aspect of the present disclosure provides a computer readable storage medium storing a computer program. When the computer program is executed by a processor, the aforementioned steps of the method for recognizing a medical entity in a medical text are performed.

BRIEF DESCRIPTION OF THE DRAWINGS

To describe technical solutions of the embodiments of the present disclosure more clearly, the accompanying drawings of the embodiments will be briefly introduced in the following. It should be known that the accompanying drawings in the following description merely involve with some embodiments of the present disclosure, but not limit the present disclosure, in which.

DETAILED DESCRIPTION

To make the technical solutions and advantages of the embodiments of the present disclosure clearer, the technical solutions in the embodiments of the present disclosure will be described clearly and completely below, in conjunction with the accompanying drawings in the embodiments of the present disclosure. Obviously, the described embodiments are merely some but not all of the embodiments of the present disclosure. All other embodiments obtained by those skilled in the art based on the described embodiments of the present disclosure without creative efforts shall fall within the protecting scope of the present disclosure.

Unless otherwise defined, all terms (including technical and scientific terms) used herein have the same meaning as commonly understood by those skilled in the art to which present disclosure belongs. It will be further understood that terms, such as those defined in commonly used dictionaries, should be interpreted as having a meaning that is consistent with their meaning in the context of the specification and will not be interpreted in an idealized or overly formal sense unless expressly so defined herein.

At present, in methods for recognizing a medical entity, attention is mainly focused on recognition of a continuous medical entity. However, a discontinuous medical entity also exists in a practical medical text. For example, in the medical text "EGD showed hiatal hernia and laceration in distal esophagus.", "hiatal hernia" and "laceration distal esophagus" are two medical entities. The "hiatal hernia" is a continuous medical entity, and the "laceration distal esophagus" is a discontinuous medical entity.

In some embodiments of the present disclosure, the method for recognizing a medical entity is described by taking an English medical text as an example. However, those skilled in the art should appreciate that a method and an apparatus for recognizing a medical entity in other languages (such as Chinese) by using the method according to some embodiments of the present disclosure also fall within the scope of protection of the present disclosure.

Figure 1:
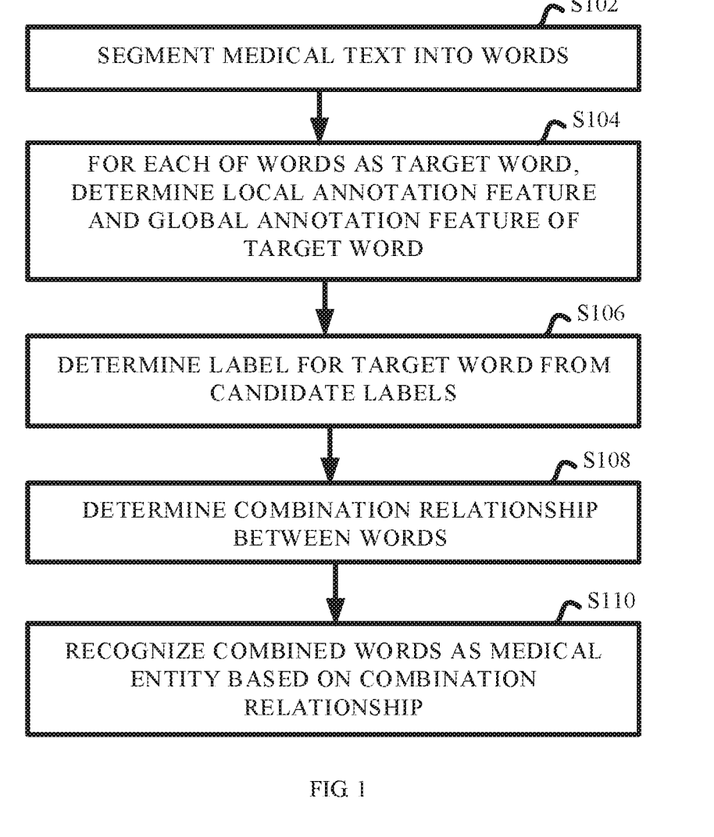
FIG. 1 is a flowchart of a method for recognizing a medical entity in a medical text according to an embodiment of the present disclosure.

FIG. 1 illustrates a flowchart of a method for recognizing a medical entity in a medical text according to an embodiment of the present disclosure.

As shown in FIG. 1, in step S102, the medical text is segmented into a plurality of words. For an English medical text, the English medical text may be segmented into a plurality of words based on spaces between the words. For a Chinese medical text, in some embodiments of the present disclosure, a lexical analysis may be performed on the inputted medical text by using a natural language processing technology to segment the medical text into a plurality of words. In some embodiments of the present disclosure, preprocessing of the medical text may be achieved by using lexical analysis algorithm and tool such as a conditional random field algorithm and a Word segmentation tool "stanford-segmenter" provided by Stanford University. In some embodiments, if the medical text includes a punctuation, the punctuation also is deemed as a word.

In step S104, for each of the plurality of words as a target word, a local annotation feature and a global annotation feature of the target word are determined.

In some embodiments of the present disclosure, the local annotation feature may include the target word. The local annotation feature may further include X previous words of the target word and X posterior words of the target word. Further, the local annotation feature may further include a part of speech of the target word, parts of speech of the X previous words of the target word, and parts of speech of the X posterior words of the target word. X here is a natural number. For example, the local annotation feature includes a target word, three previous words of the target word, three posterior words of the target word, the part of speech of the target word, parts of speech of the three previous words of the target word, and parts of speech of the three posterior words of the target word.

In some embodiments of the present disclosure, the global annotation feature may include a relationship between the target word and a recognized medical entity. The recognized medical entity may include a medical entity recognized in the current medical text, and may further include medical entities recognized in other medical texts. Further, the global annotation feature may also include a relationship between Y previous words of the target word and the recognized medical entity and a relationship between Y posterior words of the target word and the recognized medical entity. Y here is a natural number. For example, the global annotation feature includes whether the target word being contained in the recognized medical entity, whether the previous word of the target word being contained in the recognized medical entity, and whether the posterior word of the target word being contained in the recognized medical entity.

In step S106, a label for the target word is determined from a plurality of candidate labels based on the local annotation feature and the global annotation feature of the target word.

In some embodiments of the present disclosure, the plurality of candidate labels may include, for example, a first label HB, a second label DB, a third label I, a fourth label OY, and a fifth label ON. The first label HB is configured to indicate that the word is a shared beginning portion of the medical entity. The second label DB is configured to indicate that the word is an unshared beginning portion of the medical entity. The third label I is configured to indicate that the word is a successive portion of the medical entity. The fourth label OY is configured to indicate that the word is a portion of a nonmedical entity and that an operation of medical entity recognition is to be performed. The fifth label ON is configured to indicate that the word is a portion of the nonmedical entity and that the operation of medical entity recognition is not performed.

Figure 2:
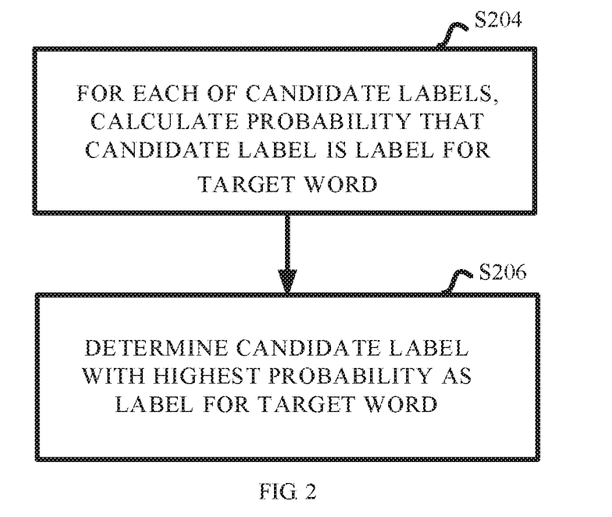
FIG. 2 is an exemplary flowchart of a process of determining a label for the target word from a plurality of candidate labels in the embodiment as shown in FIG. 1.

More specifically, FIG. 2 illustrates an exemplary process of determining a label for the target word from a plurality of candidate labels according to the embodiment as shown in FIG. 1. In the example as shown in FIG. 2, in step S204, for each of the plurality of candidate labels, a probability that the candidate label is the label for the target word is calculated. In some embodiments of the present disclosure, the probability of each of the plurality of candidate labels (for example, the plurality of labels from the first label to the fifth label) may be obtained based on the local annotation feature and the global annotation feature of the target word by means of a maximum entropy model. The maximum entropy model may be, for example, expressed as below:

$$p(c_i | x) = \frac{e^{w_i^T x}}{\sum_{j=1}^{K} e^{w_j^T x}} \quad (1)$$

wherein $w_i$ represents a parameter of an N-dimensional column vector, $1 \leq i \leq K$, K represents a total number of labels, x represents an N-dimensional feature vector of a corresponding target word, $c_i$ represents an $i^{th}$ label (in this embodiment, $c_1$ represents the first label, $c_2$ represents the second label, and so on), $p(c_i|x)$ represents the probability of determining a label as $c_i$ in the state corresponding to x. The x includes the local annotation feature and the global annotation feature of the target word. The value of dimension N of x depends on the number of parameters in the local annotation feature and the global annotation feature. In the case that one or more parameters in the local annotation feature and the global annotation feature do not exist, the absent parameter is represented by a null symbol.

In some embodiments of the present disclosure, $w_i$ may be trained by minimizing the following objective function (2):

$$L(W) = -\sum_{j=1}^{M} \log p(g_j) + \lambda \|W\|_2^2 \quad (2)$$

wherein $W \in R^{K \times N}$ represents a parameter matrix, an $i^{th}$ row of vectors in W is expressed as $w_i$, $g_j$ represents a label corresponding to a $j^{th}$ training word, $p(g_j)$ represents the probability of the label corresponding to the $j^{th}$ training word being $g_j$, M represents the number of training words, and $\lambda$ represents a coefficient of an L2 regular term, wherein $\lambda > 0$.

In the process of training the parameter matrix W having an initialized value may be preset, and x corresponding to M training words used for training is substituted into Formula (1) to obtain $p(g_j)$ of the M training words. Next, an updated W is obtained using an optimization algorithm. The process of updating W is repeated until a value of an element in W tends to be stable, and the process of training $w_i$ is over. The obtained W is substituted into Formula (1). Alternatively, the optimization algorithm may adopt a Mini-batched AdaGrad algorithm.

In step S204, the probability $p(c_i|x)$ is calculated in the case that different values are assigned to i.

In step S206, the candidate label $c_i$ with a highest probability $p(c_i|x)$ is determined as the label for the target word.

Referring back to FIG. 1, in step S108, a combination relationship between the target word and a previous word of the target word is obtained based on the label for the target word. The combination relationship includes combination and non-combination.

Figure 3:
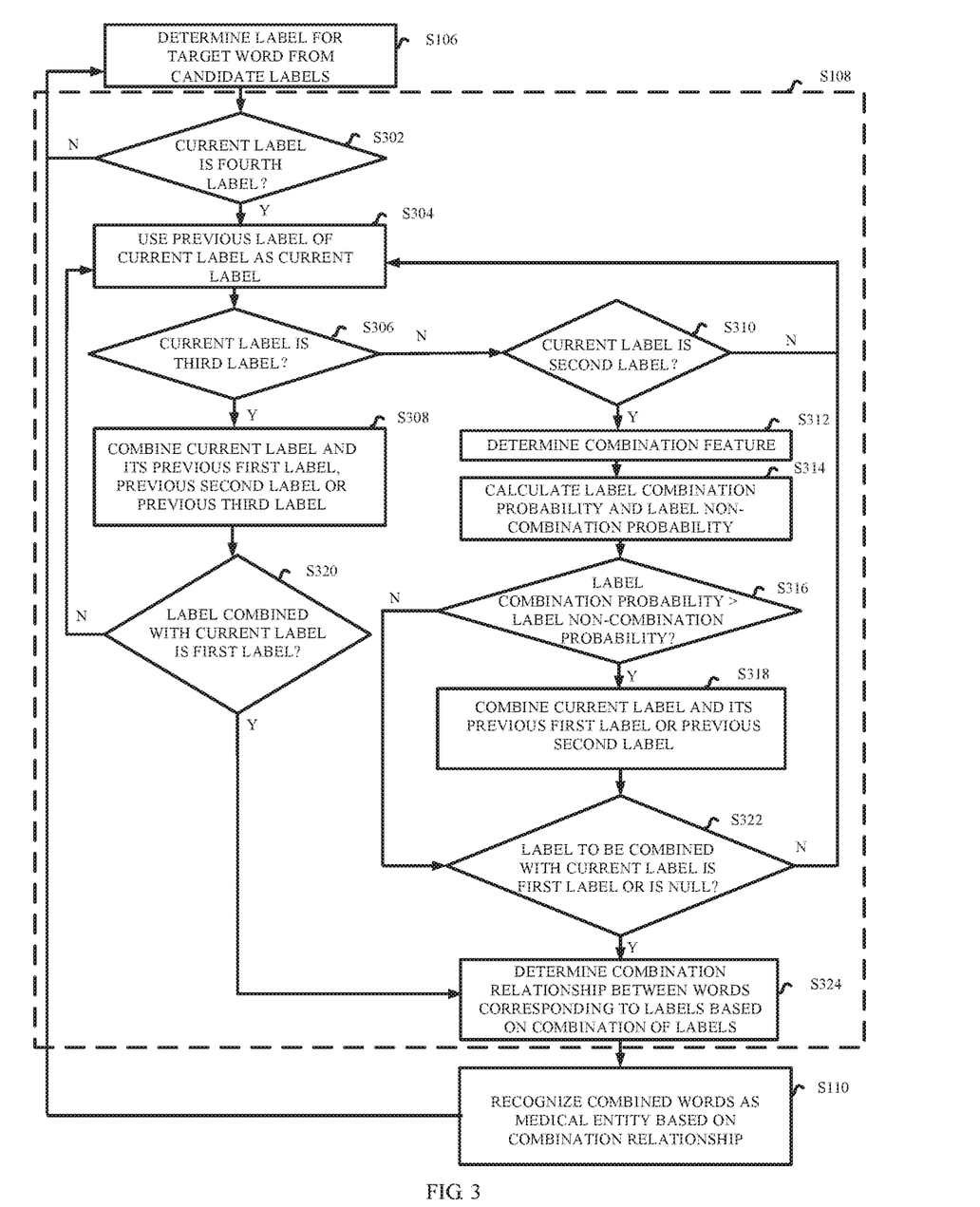
FIG. 3 is an exemplary flowchart mainly for detailed description of a process of determining a combination relationship between words in the embodiment as shown in FIG. 1.

As a more specific example of the embodiment as shown in FIG. 1, FIG. 3 illustrates, in detail, the process (S108) of determining the combination relationship between words.

After the label for the target word is determined in step S106, in step S302 it is determined whether the current label is the fourth label OY. The fourth label OY indicates that the target word is a portion of a nonmedical entity and that an operation of medical entity recognition is to be performed. If the label for the target word indicates that the operation of medical entity recognition is to be performed, it is determined the combination of the previous labels, of the label for the target word, indicating that the corresponding word can become a portion of a medical entity. The labels indicating that the corresponding word can become a portion of the medical entity includes, for example, the first label HB, the second label DB, and the third label I. If it is determined that the current label is not the fourth label OY (i.e., the determination result in step S302 is "N"), the process goes back to step S106 to further determine the label for the next word.

If it is determined that the current label is the fourth label OY (i.e., the determination result in step S302 is "Y"), the combination of the previous labels of the fourth label OY is determined.

In step S304, the previous label of the current label is used as the current label. For example, if the current label is the fourth label OY, the previous label of the fourth label OY is used as the current label.

In step S306, it may be determined whether the current label is the third label I. The third label I represents that its corresponding word is a successive portion of the medical entity. Therefore, if it is determined that the current label is the third label I (i.e., the determination result in step S306 is "Y"), the current label and a previous label of the current label are combined in step S308. Here the previous label is one of the first label HB, the second label DB, and the third label I. Next, in step S320 it is determined whether the label combined with the current label is the first label HB. The first label HB represents that its corresponding word is the very beginning portion of the medical entity. Only one first label HB may exist in one medical entity. The combination of the labels may be considered as being completed in the case that the combination of labels includes the first label HB. Therefore, if it is determined that the label combined with the current label is the first label HB (i.e., the determination result in step S320 is "Y"), in step S324 the combination relationship between words corresponding to the labels is determined based on the combination of the labels. If it is determined that the label combined with the current label is not the first label HB (i.e., the determination result in step S320 is "N"), the process goes back to step S304 to further process the previous label.

If it is determined that the current label is not the third label I (i.e., the determination result in step S306 is "N"), the process goes to step S310 to determine whether the current label is the second label DB. If it is determined that the current label is not the second label DB (i.e., the determination result in step S310 is "N"), the process goes back to step S304 to further process the previous label.

The second label DB indicates that its corresponding word is an unshared beginning portion of the medical entity. This word may be the very beginning portion of the medical entity (i.e., it is not required to be combined with the previous first label HB or the previous second label DB), or may be not the very beginning portion of the medical entity (i.e., it is required to be combined with the previous first label HB or the previous second label DB). Therefore, if the label is the second label DB, it is required to determine whether the second label DB should be combined with its previous first label HB or its previous second label DB.

In the embodiment as shown in FIG. 3, if it is determined that the current label is the second label DB (i.e., the determination result in step S310 is "Y"), a combination feature of the word (i.e., the target word) corresponding to the second label DB and a combination feature of the word corresponding to its previous first label HB or its previous second label DB are determined, in step S312. If the second label DB has neither previous first label HB nor previous second label DB, the previous label of the second label DB is defined as null.

In some embodiments of the present disclosure, the combination feature may include a morpheme contained in a corresponding word. For the Chinese medical text, the morpheme here refers to a Chinese character. Further, the combination feature may further include morphemes contained in Z previous words of the corresponding word and morphemes contained in Z posterior words of the corresponding word. Here, Z is a natural number. Thus, even though a misspelling exists in the medical text (a wrongly written character exists in the Chinese medical text), the combination feature still can provide information used for combination of the labels based on the corresponding word and correct morphemes contained in previous words of the corresponding word and correct morphemes contained in posterior words of the corresponding word. For example, the combination feature includes morphemes contained in the corresponding word, three previous words of the corresponding word, three posterior words of the corresponding word, morphemes contained in the three previous words of the corresponding word, and morphemes contained in the three posterior words of the corresponding word.

In step S314, a label combination probability and a label non-combination probability are calculated based on the combination feature of the word corresponding to the second label DB and the combination feature of the word corresponding to the previous first label HB or the previous second label DB of the second label DB. In some embodiments of the present disclosure, the label combination probability and the label non-combination probability may be calculated based on the combination feature of the word corresponding to the second label DB and the combination feature of the word corresponding to the previous first label HB or the previous second label DB of the second label DB by using a maximum entropy model (i.e., using Formula (1)). In such a case, in Formula (1), $w_i$ represents a parameter of an N-dimensional column vector (in the label annotation process and the label combination process, elements in W may be different, and number of rows K and number of columns N of W may also be different). $1 \leq i \leq K$. Here, x represents an N-dimensional feature vector of a corresponding target word, and includes the combination feature of the target word and the combination feature of the previous word, of the target word, having the first label HB or the second label DB. If one or more parameters in the combination feature are absent, the absent parameter is represented by a null symbol. In the context, $c_i$ represents whether to perform a label combination. In this embodiment, $c_1$ represents that the label combination is performed, and $c_2$ represents that the label combination is not performed. In some alternative embodiments, $c_1$ may be used to represent that the label combination is not performed, and $c_2$ may be used to represent that the label combination is performed. K is equal to 2. $p(c_i|x)$ represents the probability whether to perform a label combination in the state corresponding to x. In this embodiment, $p(c_1|x)$ represents the probability of performing a label combination in the state corresponding to x, and $p(c_2|x)$ represents the probability of not performing a label combination in the state corresponding to x. In some alternative embodiments, $p(c_1|x)$ may be used to represent the probability of not performing a label combination in the state corresponding to x, and $p(c_2|x)$ may be used to represent the probability of performing a label combination in the state corresponding to x.

In some embodiments of the present disclosure, the parameter in the maximum entropy model used for calculating the label combination probability and the label non-combination probability may also be trained by minimizing objective function (2). Different from Formula (2) used in the process of determining a label, here $g_j$ represents whether to combine the $j^{th}$ training word.

In step S316, it is determined whether the label combination probability is greater than the label non-combination probability. If it is determined that the label combination probability is not greater than the label non-combination probability (i.e., the determination result in step S316 is "N"), the second label DB and its previous first label HB or its previous second label DB are not combined. Next, the process goes to step S322 to determine whether the label combined with the current label is the first label HB or is null.

If it is determined that the label combination probability is greater than the label non-combination probability (i.e., the determination result in step S316 is "Y"), the second label DB and its previous first label HB or its previous second label DB are combined in step S318. The process goes to step S322 after the operation in step S318 is performed.

If it is determined that the label to be combined with the current label is the first label HB or is null (i.e., the determination result in step S322 is "Y"), the combination relationship between words corresponding to the labels is determined based on the combination of the labels, in step S324. If it is determined that the label to be combined with the current label is not the first label HB or is null (i.e., the determination result in step S322 is "N"), the process goes back to step S304 to further process the previous label.

After the operation in step S324 is performed, the process goes to step S110, in which the plurality of words in the medical text are combined or not combined based on the determined combination relationship between the words, and the combined words are recognized as the medical entity. In step S110, the medical entity recognized based on the words corresponding to the combination of the first label HB and the third label I or the combination of the second label DB and the third label I is a successive medical entity. The medical entity recognized based on the combination of the words corresponding to the combination of the first label HB and the second label DB is a discontinuous medical entity.

In the embodiment as shown in FIG. 3, at first it is determined whether the current label is the third label I in step S306, and then it is determined whether the current label is the second label DB in step S310. Alternatively, it is possible to firstly determine whether the current label is the second label DB, and then to determine whether the current label is the third label I. In addition, in the embodiment as shown in FIG. 3, the combination of the labels is determined by way of combining the labels from back to front (i.e., backward from the fourth label OY). Those skilled in the art should understand that in some alternative embodiments, the combination of the labels may also be determined by way of combining the labels from front to back (i.e., forward from the previous first label HB of the fourth label OY).

In some embodiments of the present disclosure, determination of the labels and combination of the labels may be implemented by way of a transition model. As a model used for describing state switching, the transition model includes, for example, but is not limited to a Markov model, a hidden Markov model, an N-gram model, and a neural network model, etc. The state of the transition model is switched from one state to another state by means of action. In some embodiments of the present disclosure, the state in the transition model is <L, E>. L represents a sequence formed by the labels, and E represents the recognized medical entity.

The action in the transition model may be, for example, {HB, DB, I, OY, ON}. If the action is OY, the medical entity recognition is performed.

Specifically, in the transition model, the probability that the candidate label is the label for the target word is calculated using the maximum entropy model, and then the label for the target word is determined by determining the highest probability. The label represents an action required to be performed in a current state. The state of the transition model is switched to a next state based on the current state and the action required to be performed. In the case that the action indicates to recognize the medical entity, the label combination probability and the label non-combination probability are calculated using the maximum entropy model, and then the combination of the labels is determined by comparing the label combination probability with the label non-combination probability. As a parameter in the state of the transition model, the medical entity recognized from the combination of the labels contributes to determining the next action required to be performed.

The method for recognizing a medical entity in a medical text according to some embodiments of the present disclosure can recognize a continuous medical entity and a discontinuous medical entity. In addition, in some embodiments of the present disclosure, a joint mode (the local annotation feature and the global annotation feature of a word are considered in the process of label annotation, and a mutual relationship between annotation and combination is considered) is adopted. Therefore, the defect of error passing in a pipeline mode (after the label annotation is completed using only the local annotation feature, the label combination is performed) may be avoided, and thus higher accuracy of medical entity recognition may be realized.

An exemplary description of the process of medical entity recognition is made below by taking "EGD showed hiatal hernia and laceration in distal esophagus." as an example.

First, the example sentence "EGD showed hiatal hernia and laceration in distal esophagus." is segmented into a plurality of words in sequence. In some embodiments of the present disclosure, words include punctuations. Therefore, this example sentence may be segmented into ten words: "EGD", "showed", "hiatal", "hernia", "and", "laceration", "in", "distal", "esophagus", and ".". Next, corresponding parts of speech are respectively annotated for the ten words. The part of speech of "." is represented by a null symbol. For example, a previous word of "EGD" is represented by a null symbol because there is no word prior to "EGD".

Next, the ten words are processed in sequence. In this example, a transition model is used for modeling and realizing the determination of label sequences and combination of the labels. The state in the transition model is <L, E>. L represents a sequence formed by the labels, and E represents the recognized medical entity. A set of actions in the transition model may be, for example, {HB, DB, I, OY, ON}. The action in the transition model represents an action (for example, labeling a next word or recognizing a medical entity) required to be performed in order to switch to a next state, based on a current state. Table 1 shows a relationship (wherein <EOS> represents that the switching process is ended) between states and actions in the transition model. In Table 1, the sequence numbers are used for illustration purposes only, and does not belong to a portion of the transition model.

TABLE 1

| Sequence numbers | States | Actions |
|---|---|---|
| S1 | ... | ... |
| S2 | <(ON, ON, DB, I), { }> | OY |
| S3 | <(ON, ON, DB, I, OY), {hiatal hernia}> | HB |
| S4 | <(ON, ON, DB, I, OY, HB), {hiatal hernia}> | ON |
| S5 | <(ON, ON, DB, I, OY, HB, ON), {hiatal hernia}> | DB |
| S6 | <(ON, ON, DB, I, OY, HB, ON, DB), {hiatal hernia}> | I |
| S7 | <(ON, ON, DB, I, OY, HB, ON, DB, I), {hiatal hernia}> | OY |
| S8 | <(ON, ON, DB, I, OY, HB, ON, DB, I, OY), {hiatal hernia, laceration distal esophagus}> | <EOS> |

For "EGD", based on Formula (1), the probability of the candidate label being the label for "EGD" is calculated as below: $P1=p(c_1|x)$, $P2=p(c_2|x)$, $P3=p(c_3|x)$, $P4=p(c_4|x)$, and $P5=p(c_5|x)$. Here, $c_1$ represents the first label HB, $c_2$ represents the second label DB, $c_3$ represents the third label I, $c_4$ represents the fourth label OY, and $c_5$ represents the fifth label ON. x represents an N-dimensional feature vector including the local annotation feature and a global annotation feature of the "EGD". In x, morphemes in the local annotation feature and the global annotation feature are switched to N corresponding numerical values. It is known that the value of P5 is the maximum value by comparing P1, P2, P3, P4, and P5. Therefore, the label for "EGD" is determined as the fifth label ON.

Similarly, the label ON for "showed", the label DB for "hiatal", and the label I for "hernia" may be obtained. Now, the transition model is in the state S2.

For "and", its label is determined as OY (that is, the action corresponding to the state S2 is OY). In the case that the transition model adopts the action OY, the transition model performs the action of medical entity recognition. The labels ON for "EGD" and "showed" indicate that the respective target word is a portion of a nonmedical entity and that an operation of medical entity recognition is not to be performed. Therefore, it may be directly determined that the labels ON for "EGD" and "showed" and previous labels thereof are not combined. The label DB for "hiatal" represents an unshared beginning portion of the medical entity. The label DB is not combined with its previous label because no label HB exists prior to "hiatal". The label I for "hernia" represents a successive portion of the medical entity, and thus the label I of "hernia" is combined with the label DB of "hiatal". In this way, a combination of the labels DB and I is obtained. A combination of words "hiatal hernia" corresponding to the combination of the labels DB and I is recognized as the medical entity (the medical entity is a continuous medical entity).

Next, for "laceration", $P1=p(c_1|x)$, $P2=p(c_2|x)$, $P3=p(c_3|x)$, $P4=p(c_4|x)$, and $P5=p(c_5|x)$ are calculated based on Formula (1). It is determined that the value of P1 is the highest by comparing P1, P2, P3, P4, and P5. Therefore, it is determined that the label for "laceration" is the first label HB.

Similarly, the label ON for "in", the label DB for "distal", and the label I for "esophagus" are obtained. For ".", its label is determined as OY (that is, the action corresponding to the state S7 is OY). In the case that the transition model adopts the action OY, the transition model performs the action of medical entity recognition. The label HB for "laceration" represents the very beginning portion of the medical entity, and thus the label HB is not combined with a previous label thereof. The label ON for "in" indicates that the target word is a portion of the nonmedical entity and that the operation of medical entity recognition is not performed. Therefore, it may be directly determined that the label ON is not combined with a previous label thereof. The label DB for "distal" represents the unshared beginning portion of the medical entity. Therefore, it is required to determine whether to combine the label DB for "distal" with its previous first label HB or its previous second label DB (the label HB for "laceration" here). Here, the label combination probability $P1=p(c_1|x)$ and the label non-combination probability $P2=p(c_2|x)$ are calculated still using Formula (1). $c_1$ represents to perform label combination, and $c_2$ represents not to perform label combination. x represents an N-dimensional feature vector corresponding to "distal", and includes the combination feature of "distal" and the combination feature (here the combination feature of "laceration") of the previous word of "distal" having the first label or the second label. In the case that P1 is greater than P2, it is determined that the label HB for "laceration" and the label DB for "distal" should be combined. The combination feature is related to morphemes contained in the corresponding word and a previous word and a posterior word of the corresponding word. Therefore, for example, in the case that "laceration" is misspelt into "lacerasion", the probability of combining the morphemes "lacera" and "distal" can help to enhance the probability of combining "lacerasion" and "distal".

The label I for "esophagus" represents a successive portion of the medical entity. Therefore, the label I for "esophagus" is combined with the label DB for "distal".

In this way, the combination of the labels HB, DB, and I is obtained. The combination of words "laceration distal esophagus" corresponding to the combination of the labels HB, DB, and I is recognized as the medical entity (the medical entity is a discontinuous medical entity).

Figure 4:
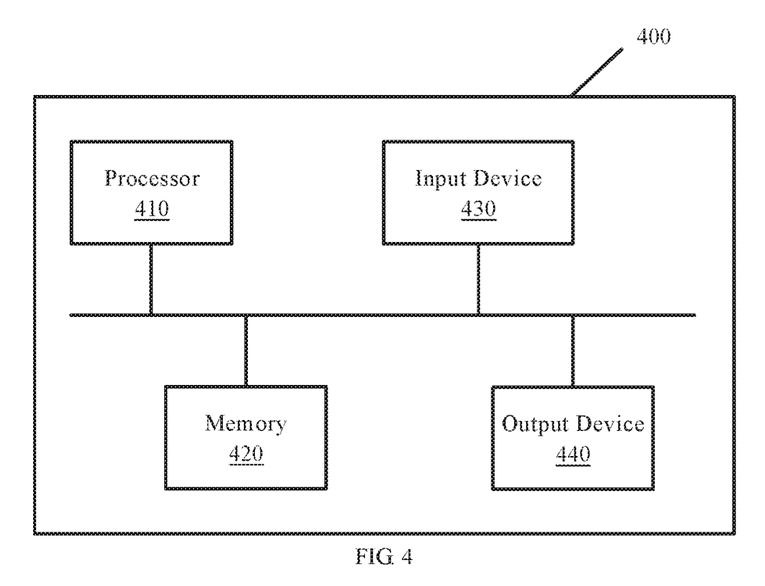
FIG. 4 is a schematic block diagram of an apparatus for recognizing a medical entity in a medical text according to an embodiment of the present disclosure.

FIG. 4 illustrates a schematic block diagram of an apparatus 400 for recognizing a medical entity in a medical text according to an embodiment of the present disclosure. As shown in FIG. 4, the apparatus 400 may include a processor 410 and a memory 420 storing a computer program. When the computer program is executed by the processor 410, the apparatus 400 is caused to perform the steps of the method for recognizing a medical entity in a medical text as shown in FIG. 1. That is, the apparatus 400 may segment the medical text into a plurality of words. Each of the plurality of words is used as a target word. For a target word, a local annotation feature and a global annotation feature of the target word are determined. The local annotation feature includes the target word, and the global annotation feature includes a relationship between the target word and the recognized medical entity. Next, a label for the target word is determined from a plurality of candidate labels based on the local annotation feature and the global annotation feature of the target word. Next, a combination relationship between the target word and a previous word of the target word is obtained based on the label for the target word. The combination relationship includes combination and non-combination. Next, the combined words are recognized as the medical entity based on the combination relationship.

In some embodiments of the present disclosure, the processor 410 may be, for example, a central processing unit (CPU), a microprocessor, a digital signal processor (DSP), a processor based on a multi-core processor architecture, and so on. The memory 420 may be a memory of any type that is implemented by using a text storage technology, including but not limited to a random access memory, a read-only memory, a semiconductor-based memory, a flash memory, a magnetic disk memory, and so on.

Furthermore, in some embodiments of the present disclosure, the apparatus 400 also may include an input device 430 such as a keyboard or a mouse to input the medical text. Moreover, the apparatus 400 may also include an output device 440 such as a display to output the recognized medical entity.

In some embodiments of the present disclosure, the apparatus 400 determines the label for the target word from the plurality of candidate labels based on the local annotation feature and the global annotation feature of the target word by calculating, for each of the plurality of candidate labels, a probability that the candidate label is the label for the target word based on the local annotation feature and the global annotation feature of the target word. Next, the candidate label with a highest probability is determined as the label for the target word.

In some embodiments of the present disclosure, the apparatus 400 obtains a combination relationship between the target word and a previous word of the target word based on the label for the target word by performing no combination of the label and a previous label of the label if the label is a first label HB, combining the label and one of a previous first label HB, a previous second label DB, and a previous third label I of the label if the label is the third label I, if the label is the second label DB, determining a combination feature of the target word and a combination feature of a previous word of the target word having the first label HB or the second label DB, wherein the combination feature includes a morpheme contained in the corresponding word, calculating a label combination probability and a label non-combination probability based on the combination feature of the target word and the combination feature of the previous word of the target word having the first label HB or the second label DB, combining the second label DB and a previous first label HB or a previous second label DB of the second label DB in response to the label combination probability being greater than the label non-combination probability, performing no combination of the second label and the previous first label or the previous second label of the second label in response to the label combination probability being not greater than the label non-combination probability, performing no combination of the label and the previous label of the label and performing the operation of medical entity recognition if the label is the fourth label OY, performing no combination of the label and the previous label of the label if the label is the fifth label ON, and determining the combination relationship between the words corresponding to the labels based on the combination of the labels.

Other embodiments of the present disclosure also provide a computer readable storage medium storing a computer program. When the computer program is executed by a processor, the steps of the method for recognizing a medical entity in a medical text as shown in FIG. 1 are performed.

As used herein and in the appended claims, the singular form of a word includes the plural, and vice versa, unless the context clearly dictates otherwise. Thus, singular words are generally inclusive of the plurals of the respective terms. Similarly, the words "include" and "comprise" are to be interpreted as inclusively rather than exclusively. Likewise, the terms "include" and "or" should be construed to be inclusive, unless such an interpretation is clearly prohibited from the context. Where used herein the term "examples," particularly when followed by a listing of terms is merely exemplary and illustrative, and should not be deemed to be exclusive or comprehensive.

Further adaptive aspects and scopes become apparent from the description provided herein. It should be understood that various aspects of the present disclosure may be implemented separately or in combination with one or more other aspects. It should also be understood that the description and specific embodiments in the present disclosure are intended to describe rather than limit the scope of the present disclosure.

A plurality of embodiments of the present disclosure has been described in detail above. However, apparently those skilled in the art may make various modifications and variations on the embodiments of the present disclosure without departing from the spirit and scope of the present disclosure. The scope of protecting of the present disclosure is limited by the appended claims.

What is claimed is:

1. A computer-implemented method for recognizing a medical entity in a medical text, the method comprising:
   segmenting, by at least one processor using lexical analysis, the medical text into a plurality of words;
   performing, by at least one processor, the following operations on each of the plurality of words as a target word:
      determining, by at least one processor using parts of speech analysis, a local annotation feature and a global annotation feature of the target word, wherein the local annotation feature comprises the target word, and wherein the global annotation feature comprises a relationship between the target word and a recognized medical entity;
      determining, by at least one processor using a maximum entropy model, a label for the target word from a plurality of candidate labels based on the local annotation feature and the global annotation feature of the target word;
      obtaining, by at least one processor using morphological analysis, a combination relationship between the target word and a previous word of the target word based on the label for the target word, wherein the combination relationship comprises combination and non-combination; and
      recognizing, by at least one processor, the combined words as the medical entity based on the combination relationship,
   wherein the plurality of candidate labels comprise:
      a first label configured to indicate that the word is a shared beginning portion of the medical entity;
      a second label configured to indicate that the word is an unshared beginning portion of the medical entity;
      a third label configured to indicate that the word is a successive portion of the medical entity;
      a fourth label configured to indicate that the word is a portion of a nonmedical entity and that an operation of medical entity recognition is to be performed; and a fifth label configured to indicate that the word is a portion of the nonmedical entity and that the operation of medical entity recognition is not performed.

2. The method according to claim 1, wherein determining the label for the target word from the plurality of candidate labels based on the local annotation feature and the global annotation feature of the target word comprises:
calculating, for each of the plurality of candidate labels, a probability that the candidate label is the label for the target word based on the local annotation feature and the global annotation feature of the target word; and
determining the candidate label with a highest probability as the label for the target word.

3. The method according to claim 2, wherein the probability is calculated using a maximum entropy model.

4. The method according to claim 3, wherein the maximum entropy model is trained using an optimization algorithm.

5. The method according to claim 1, wherein obtaining the combination relationship between the target word and the previous word of the target word based on the label for the target word comprises:
performing no combination of the label and a previous label of the label if the label is the first label;
combining the label and one of a previous first label, a previous second label and a previous third label of the label if the label is the third label,
if the label is the second label:
  determining a combination feature of the target word and a combination feature of a previous word of the target word having the first label or the second label, wherein the combination feature comprises a morpheme contained in a corresponding word;
  calculating a label combination probability and a label non-combination probability based on the combination feature of the target word and the combination feature of the previous word of the target word having the first label or the second label;
  combining the second label and a previous first label or a previous second label of the second label in response to the label combination probability being greater than the label non-combination probability; and
  performing no combination of the second label and the previous first label or the previous second label of the second label in response to the label combination probability being not greater than the label non-combination probability;
performing no combination of the label and the previous label of the label and performing the operation of medical entity recognition if the label is the fourth label;
performing no combination of the label and the previous label of the label if the label is the fifth label; and
determining the combination relationship between the words corresponding to the labels based on the combination of the labels.

6. The method according to claim 5, wherein the combination feature further comprises morphemes contained in Z previous words of the corresponding word and morphemes contained in Z posterior words of the corresponding word, and wherein Z is a natural number.

7. The method according to claim 6, wherein the combination feature comprises morphemes contained in the corresponding word, Z previous words of the corresponding word, Z posterior words of the corresponding word, morphemes contained in the Z previous words of the corresponding word, and morphemes contained in the Z posterior words of the corresponding word.

8. The method according to claim 5, wherein the label combination probability and the label non-combination probability are calculated using a maximum entropy model.

9. The method according to claim 1, wherein the local annotation feature further comprises X previous words of the target word and X posterior words of the target word, wherein X is a natural number.

10. The method according to claim 9, wherein the local annotation feature further comprises a part of speech of the target word, parts of speech of the X previous words of the target word, and parts of speech of the X posterior words of the target word.

11. The method according to claim 1, wherein the global annotation feature further comprises i) a relationship between Y previous words of the target word and the recognized medical entity and ii) a relationship between Y posterior words of the target word and the recognized medical entity, and wherein Y is a natural number.

12. The method according to claim 11, wherein the global annotation feature comprises whether the target word is contained in the recognized medical entity, whether the Y previous words of the target word are contained in the recognized medical entity, and whether the Y posterior words of the target word are contained in the recognized medical entity.

13. An apparatus for recognizing a medical entity in a medical text, the apparatus comprising:
at least one processor; and
at least one memory storing a computer program;
wherein the computer program is executable by the at least one processor, whereby the apparatus is configured to:
  use lexical analysis to segment the medical text into a plurality of words;
  perform the following operations on each of the plurality of words as a target word:
    use parts of speech analysis to determine a local annotation feature and a global annotation feature of the target word, wherein the local annotation feature comprises the target word, and wherein the global annotation feature comprises a relationship between the target word and a recognized medical entity;
    use a maximum entropy model to determine a label for the target word from a plurality of candidate labels based on the local annotation feature and the global annotation feature of the target word;
    use morphological analysis to obtain a combination relationship between the target word and a previous word of the target word based on the label for the target word, wherein the combination relationship comprises combination and non-combination; and
    recognize the combined word as the medical entity based on the combination relationship,
  wherein the plurality of candidate labels comprise:
    a first label configured to indicate that the word is a shared beginning portion of the medical entity;
    a second label configured to indicate that the word is an unshared beginning portion of the medical entity;
    a third label configured to indicate that the word is a successive portion of the medical entity;

a fourth label configured to indicate that the word is a portion of a nonmedical entity and that an operation of medical entity recognition is to be performed; and a fifth label configured to indicate that the word is a portion of the nonmedical entity and that the operation of medical entity recognition is not performed.

14. The apparatus according to claim 13, wherein the apparatus is configured to determine the label for the target word from the plurality of candidate labels based on the local annotation feature and the global annotation feature of the target word by:

calculating, for each of the plurality of candidate labels, a probability that the candidate label is the label for the target word based on the local annotation feature and the global annotation feature of the target word; and determining the candidate label with a highest probability as the label for the target word.

15. The apparatus according to claim 13, wherein the apparatus is configured to obtain the combination relationship between the target word and the previous word of the target word based on the label for the target word by:

performing no combination of the label and a previous label of the label if the label is the first label;

combining the label and one of a previous first label, a previous second label and a previous third label of the label if the label is the third label;

if the label is the second label:

determining a combination feature of the target word and a combination feature of a previous word of the target word having the first label or the second label, wherein the combination feature comprises a morpheme contained in a corresponding word;

calculating a label combination probability and a label non-combination probability based on the combination feature of the target word and the combination feature of the previous word of the target word having the first label or the second label;

combining the second label and a previous first label or a previous second label of the second label in response to the label combination probability being greater than the label non-combination probability; and performing no combination of the second label and the previous first label or the previous second label of the second label in response to the label combination probability being not greater than the label non-combination probability;

performing no combination of the label and the previous label of the label and performing the operation of medical entity recognition if the label is the fourth label;

performing no combination of the label and the previous label of the label if the label is the fifth label; and determining the combination relationship between the words corresponding to the labels based on the combination of the labels.

16. The apparatus according to claim 15, wherein the combination feature further comprises morphemes contained in Z previous words of the corresponding word and morphemes contained in Z posterior words of the corresponding word, and wherein Z is a natural number.

17. The apparatus according to claim 13, wherein the local annotation feature further comprises X previous words of the target word and X posterior words of the target word, and wherein X is a natural number.

18. The apparatus according to claim 13, wherein the global annotation feature further comprises i) a relationship between Y previous words of the target word and the recognized medical entity and ii) a relationship between Y posterior words of the target word and the recognized medical entity, and wherein Y is a natural number.

* * * * *

UNITED STATES PATENT AND TRADEMARK OFFICE
CERTIFICATE OF CORRECTION

| | |
|---|---|
| PATENT NO. | : 11,586,809 B2 |
| APPLICATION NO. | : 16/316468 |
| DATED | : February 21, 2023 |
| INVENTOR(S) | : Zhenzhong Zhang |

It is certified that error appears in the above-identified patent and that said Letters Patent is hereby corrected as shown below:

In the Specification

Column 6, Line 36, delete "training the parameter" and insert therefor -- training wi, the parameter --.
Column 11, Table 1, Line 5, delete "hiatal hemia" and insert therefor -- hiatal hernia --.
Column 11, Table 1, Line 6, delete "hiatal hemia" and insert therefor -- hiatal hernia --.
Column 11, Table 1, Line 8, delete "hiatal hemia" and insert therefor -- hiatal hernia --.

Signed and Sealed this
Second Day of May, 2023

Katherine Kelly Vidal
*Director of the United States Patent and Trademark Office*